US00PP27593P3

(12) United States Plant Patent
Travers

(10) Patent No.: US PP27,593 P3
(45) Date of Patent: Jan. 24, 2017

(54) ***CLEMATIS* PLANT NAMED 'TRAJEM'**

(50) Latin Name: ***Clematis* hybrid**
Varietal Denomination: TRAJEM

(71) Applicant: Bernard Travers, Saint Cyr en Val (FR)

(72) Inventor: Bernard Travers, Saint Cyr en Val (FR)

( * ) Notice: Subject to any disclaimer, the term of this patent is extended or adjusted under 35 U.S.C. 154(b) by 88 days.

(21) Appl. No.: 14/544,076

(22) Filed: Nov. 24, 2014

(65) Prior Publication Data

US 2016/0150706 P1 May 26, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

UPOV—International Union for the Protection of New Varieties of Plants, PLUTO:Plant Variety Database; Apr. 14, 2016; citation for 'Trajem' (1 pg total).*

* cited by examiner

*Primary Examiner* — Susan McCormick Ewoldt
(74) *Attorney, Agent, or Firm* — Cassandra Bright

(57) ABSTRACT

A new and distinct *Clematis* hybrid named 'TRAJEM' is disclosed, characterized by a unique, very large diameter flowers. Foliage is ternate, and above average in length. Flowers are violet in color, with a pink median line. The new cultivar is a *Clematis* typically suited for ornamental container and landscape use.

1 Drawing Sheet

Latin name of the genus and species: *Clematis* hybrid.
Variety denomination: 'TRAJEM'.

BACKGROUND OF THE INVENTION

The new cultivar is the result of a breeding program, with the objective to develop new varieties of *Clematis* with strong growth and interesting flowers for commercial purposes. The new variety was discovered as a single plant among a group of seedlings of unknown parentage observed by the inventor, Bernard Travers. The discovery was made during 2004. Discovery was made at a commercial nursery in Orleans, France.

After selecting and isolating the new cultivar, asexual reproduction of the new cultivar 'TRAJEM' was first performed at a commercial nursery in St. Jean Le Blanc by vegetative cuttings during 2005. The inventor maintained the original plant, and observed the clones for several years, to establish stability of the characteristics. 'TRAJEM' has since produced multiple generations and has shown that the unique features of this cultivar are stable and reproduced true to type. Public access to plant material first occurred during early Spring of 2014. Before this time, plant material was under the control of the inventor, or those directly authorized by the inventor and no enabling access to plant material occurred. This variety has been applied for Plant Breeder's Right's Protection in the EU, with CPVO application number 2013/1737. A copy of the technical questionnaire is included with the mailing of this application. A grant has not yet issued, and technical exam process has not been completed. Neither the EU application, nor any other publication resulted in an enabling disclosure of 'TRAJEM'.

SUMMARY OF THE INVENTION

The cultivar 'TRAJEM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TRAJEM.' These characteristics in combination distinguish 'TRAJEM' as a new and distinct *Clematis* cultivar:

1. Large flowers: 17 to 20 cm in diameter.
2. Violet tepals with Light pink Median line
3. Lightly wavy tepals
4. Light yellow stamens
5. Large leaves: up to 26 cm

PARENTAL COMPARISON

Parent varieties are unknown, the breeder is unable to supply records of the crossings.

COMMERCIAL COMPARISON

Plants of the new cultivar 'TRAJEM' can be compared to the known commercial variety *Clematis* hybrid 'Kacpur' unpatented. The *Clematis* varieties have similar large sized flowers. and produce similar amounts of tepals. 'TRAJEM' differs from 'Kacpur in the following:

1. 'TRAJEM' Violet colored tepals with a light pink median line. The comparator has dark purple tepals with a medium pink median line.
2. 'TRAJEM' has creamy yellow stamens and anthers. 'Kacpur' has white stamens with dark purple anthers.
3. 'TRAJEM' produces foliage up to 26 cm long. Foliage of 'Kacpur' is typically around 13 cm long.

Plants of the new cultivar 'TRAJEM' can be compared to the known commercial variety *Clematis* 'Haku Ookan', unpatented. The *Clematis* varieties have similar flower color and produce similar amounts of tepals. 'TRAJEM' differs from the comparator in the following:

1. 'TRAJEM' has a different tepal than 'Haku Ookan'.
2. 'TRAJEM' has Violet flowers, whereas flowers of 'Haku Ookan' are darker colored and more Violet-Blue.
3. 'TRAJEM' produces a larger flower.
4. Plants of 'TRAJEM' are shorter at maturity than plants of 'Haku Ookan'.

BRIEF DESCRIPTION OF THE PHOTOGRAPH

The accompanying photograph in FIG. 1 illustrates in full color a typical flowers and foliage of 'TRAJEM'. This plant is approximately 8 months old, grown in an approximately 3 gallon nursery container.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'TRAJEM' plants grown outdoors in Saint Cyr en Val, France. The growing temperature ranged from approximately −2° C. to 25° C. at night to 8° C. to 33° C. during the day. No artificial light, photoperiodic treatments or chemical treatments were given to the plants. Measurements and numerical values represent averages of typical flowering types.

Botanical classification: *Clematis* hybrid 'TRAJEM'.

Age of the plant described: Approximately 8 months.

PROPAGATION

Typical method: Vegetative cuttings.

Time to initiate rooting: Approximately 20 days at 21° C. or higher.

Time to produce a rooted plantlet: Approximately 40 days at 20° C. or higher.

Root description: Fine, fibrous.

PLANT

Growth habit: Climbing vine.

Height: Approximately 150 cm.

Plant spread: Approximately 100 cm.

Growth rate: Moderate. During active growing season in Spring, approximately 70 cm per month.

Branching characteristics: One main stem.

Length of main stem: Approximately 100 cm.

Diameter of main stem: Approximately 0.2 to 0.5 cm.

Main stem color: Near RHS Yellow-Green 144C, slight flushing with Greyed-Orange 173C.

Main stem texture: Glabrous.

Internode length: Approximate range 6 cm to 15 cm.

Strength: Strong, flexible, semi-woody.

FOLIAGE

*Arrangement*.—Opposite, mostly compound trifoliate occasionally single.

*Overall leaf length*.—Up to 26 cm long.

*Overall leaf diameter*.—Approximately 15 cm.

*Leaflets*.—Average Length: approximately 9.5 cm. Average Width: approximately 4.5 cm. Shape of blade: Lanceolate. Apex: Acute. Base: Cordate to obtuse.

*Attachment*.—Stalked, twining leaf petiole.

*Margin*.—Entire.

*Texture of upper surface*.—Smooth with distinctly hirsute veins.

*Texture of lower surface*.—Rugose, slightly pubescent toward margin.

*Color*.—Young foliage upper side: Near RHS Green 143C. Young foliage under side: Near RHS Yellow-Green 144A . Mature foliage upper side: Near RHS Green 143A. Mature foliage under side: Near RHS Green 143B.

*Venation*.—Type: Pinnate. Venation color upper side: Near RHS Yellow-Green 144A. Venation color under side: Near RHS Yellow-Green 144A.

Petiole:

*Length*.—Range from 5.0 to 6.5 cm.

*Diameter*.—Approximately 0.1 to 0.3 cm.

*Texture*.—Hirsute.

*Color*.—Near RHS Green 143C, with Greyed-Orange 163C.

FLOWER

Bloom period:

*Natural season*.—First flush of flowers occurs during May and June, with an abundance of flowering. A secondary flush, with less flowering occurs in September.

Inflorescence type and habit: Single occurring, axillary; flowers facing outward.

Flower fragrance: None.

Rate of flower opening: Approximately 7 days from bud to fully opened flower.

Flower longevity on plant: Approximately 8 to 12 days, after fully opened. Self-cleaning.

Inflorescence size:

*Diameter*.—Average 17 to 20 cm.

*Depth*.—Average 7.0 cm.

Corolla:

*Tepal arrangement*.—Single whorl, overlapping.

*Quantity*.—8 per flower.

*Shape*.—Obovate.

*Size*.—Length: Average 8.0 to 9.5 cm. Width: Average 3.3 cm.

*Margin*.—Very slightly crenate, moderate undulation.

*Apex*.—Acute.

*Base*.—Truncate.

*Texture*.—Smooth, velvety.

Color:

*Tepals*.—When opening: Upper surface: Near RHS Violet N87B with median line near Red-Purple 69B. Lower surface: Near RHS Violet N87B, streaked Purple 76B. Fully opened: Upper surface: Near RHS Violet N87C with median line near Red-Purple 69B. Lower surface: Near RHS Violet N87C, streaked Purple 76B. Ageing: Upper surface: Near RHS Violet N87D with median line near Red-Purple 69D. Lower surface: Near RHS Violet N87C, streaked Purple 76D.

Bud:

*Shape*.—Elongated sphere.
*Length*.—Approximately 17 cm.
*Diameter*.—Approximately 7.5 cm.
*Color*.—Near RHS Violet N87D, flushed Violet N87A at apex.

Pedicels:

*Length*.—Average range 10 to 18 cm.
*Width*.—Approximately 0.4 cm.
*Angle*.—Average 45° to 80°.
*Strength*.—Flexible.
*Color*.—Near RHS Green 143C.

REPRODUCTIVE ORGANS

Stamens:

*Number*.—Average 120 per flower.
*Anther length*.—Approximately 0.5 cm.
*Anther color*.—Near RHS Yellow-White 158A.
*Anther shape*.—Oblong.
*Filament length*.—Approximately 1.9.
*Filament color*.—Near RHS Yellow-White 158C.
*Pollen quantity*.—Moderate.
*Pollen color*.—Greyed-Yellow 161D.

Pistil:

*Length*.—Approximately 2.7 cm.
*Style length*.—Approximately 1.1 cm.
*Stigma*.—Shape: Fine irregular hairs. Color: Near RHS Green-White 157B.

OTHER CHARACTERISTICS

Seeds: Seed production not observed.

Disease/pest resistance: Neither resistance nor susceptibility to normal diseases and pests of *Clematis* has been observed.

Temperature tolerance: Tolerates temperatures from approximately −20° C. to 45° C.

What is claimed is:

1. A new and distinct cultivar of *Clematis* hybrid plant named 'TRAJEM' as herein illustrated and described.

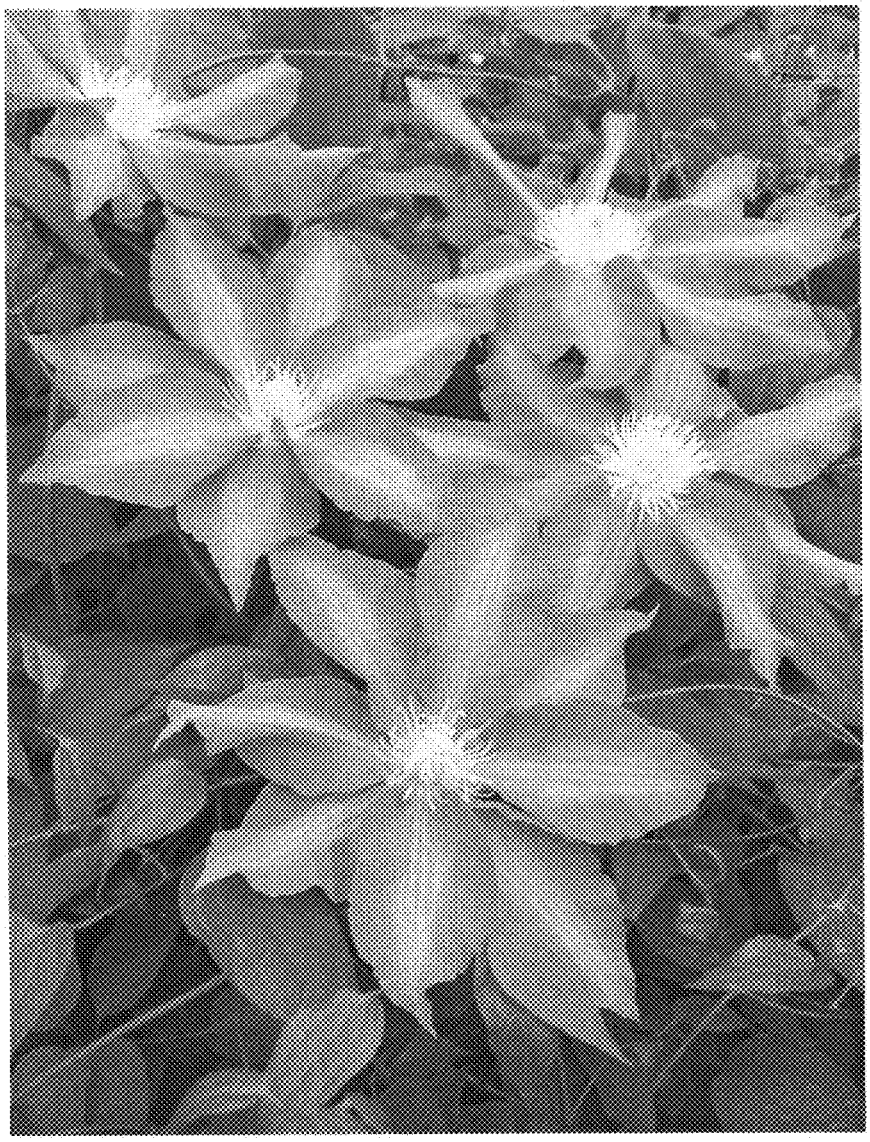

* * * * *